United States Patent [19]

Warner et al.

[11] Patent Number: 5,326,376
[45] Date of Patent: Jul. 5, 1994

[54] FEMORAL STEM PROSTHESIS

[75] Inventors: David B. Warner; Leslie N. Gilbertson; Gregory S. Meadows, all of Warsaw; Kenneth S. Shipp, Winona Lake, all of Ind.

[73] Assignee: Zimmer, Inc., Warsaw, Ind.

[21] Appl. No.: 110,741

[22] Filed: Aug. 23, 1993

[51] Int. Cl.⁵ .................... A61F 2/32; A61F 2/36
[52] U.S. Cl. ............................. 623/23; 606/93
[58] Field of Search ................ 623/16, 18, 20, 23, 623/22; 606/93

[56] References Cited

U.S. PATENT DOCUMENTS

| | | | |
|---|---|---|---|
| Re. 32,488 | 9/1987 | Gustilo et al. | 623/23 |
| 3,073,022 | 1/1963 | Bush et al. | 29/553 |
| 3,531,964 | 10/1970 | Manning et al. | 72/53 |
| 3,643,658 | 2/1972 | Steinemenan | 128/92 D |
| 3,754,976 | 8/1973 | Babecki et al. | 117/105 |
| 3,793,650 | 2/1974 | Sydney et al. | 3/1 |
| 3,829,904 | 8/1974 | Sydney et al. | 3/1 |
| 3,939,496 | 2/1976 | Sydney et al. | 3/1.91 |
| 4,040,129 | 8/1977 | Steinemann et al. | 3/1.9 |
| 4,135,283 | 1/1979 | Kohlhage | 29/173 |
| 4,226,111 | 10/1980 | Wahli | 72/437 |
| 4,589,883 | 5/1986 | Kenna | 623/22 |
| 4,612,920 | 9/1986 | Lower | 128/92 |
| 4,629,631 | 12/1986 | Dearnaley | 427/38 |
| 4,687,487 | 8/1987 | Hintermann | 623/18 |
| 4,693,760 | 9/1987 | Sioshansi | 148/4 |
| 4,855,026 | 8/1989 | Sioshansi | 204/192.11 |
| 4,855,101 | 8/1989 | Mohs et al. | 419/8 |
| 4,865,608 | 9/1989 | Brooker, Jr. | 623/23 |
| 5,047,035 | 9/1991 | Mikhail et al. | 606/93 |
| 5,057,108 | 10/1991 | Shetty et al. | 606/53 |
| 5,080,680 | 1/1992 | Mikhail et al. | 623/16 |
| 5,108,405 | 4/1992 | Mikhail et al. | 606/79 |
| 5,171,275 | 12/1992 | Ling et al. | 623/16 |
| 5,171,288 | 12/1992 | Mikhail et al. | 623/23 |
| 5,192,283 | 3/1993 | Ling et al. | 606/93 |
| 5,192,323 | 3/1993 | Shetty et al. | 623/16 |

FOREIGN PATENT DOCUMENTS

| | | |
|---|---|---|
| 0449793A1 | 10/1991 | European Pat. Off. . |
| 0470778A1 | 2/1992 | European Pat. Off. . |
| 0472315A1 | 2/1992 | European Pat. Off. . |
| 1409054 | 9/1971 | United Kingdom . |

Primary Examiner—David Isabella
Attorney, Agent, or Firm—Todd A. Dawson

[57] ABSTRACT

A tapered, collarless femoral hip joint prosthesis formed of a surface hardened titanium alloy having a highly polished surface is provided.

3 Claims, 2 Drawing Sheets

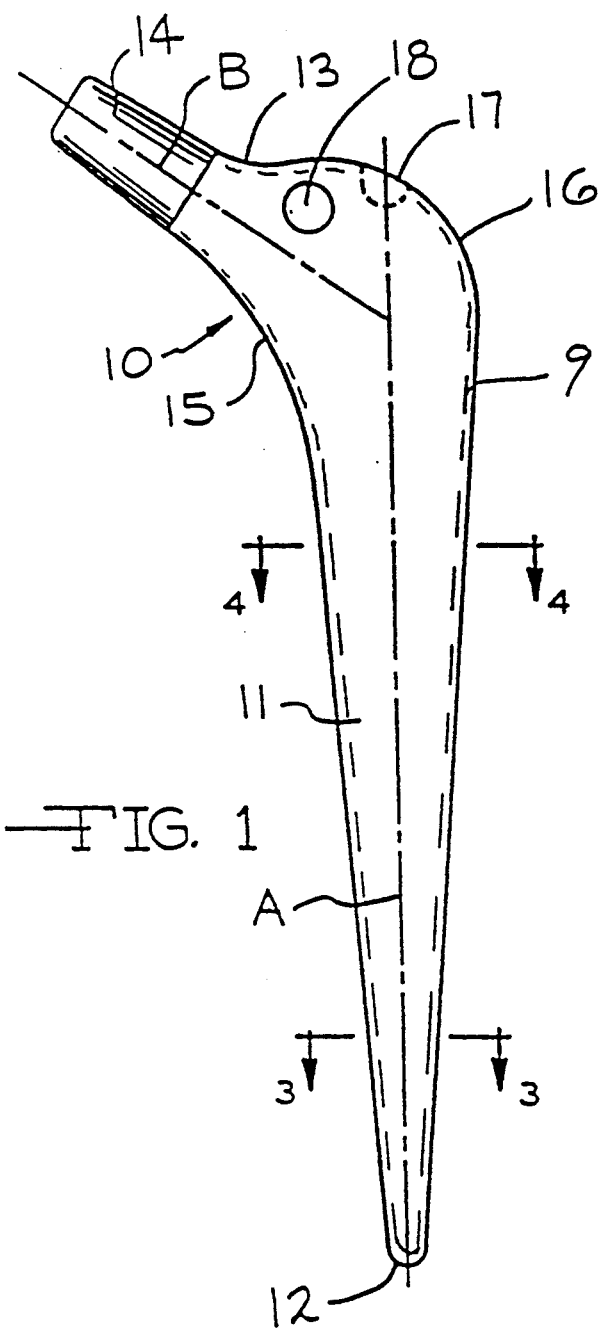
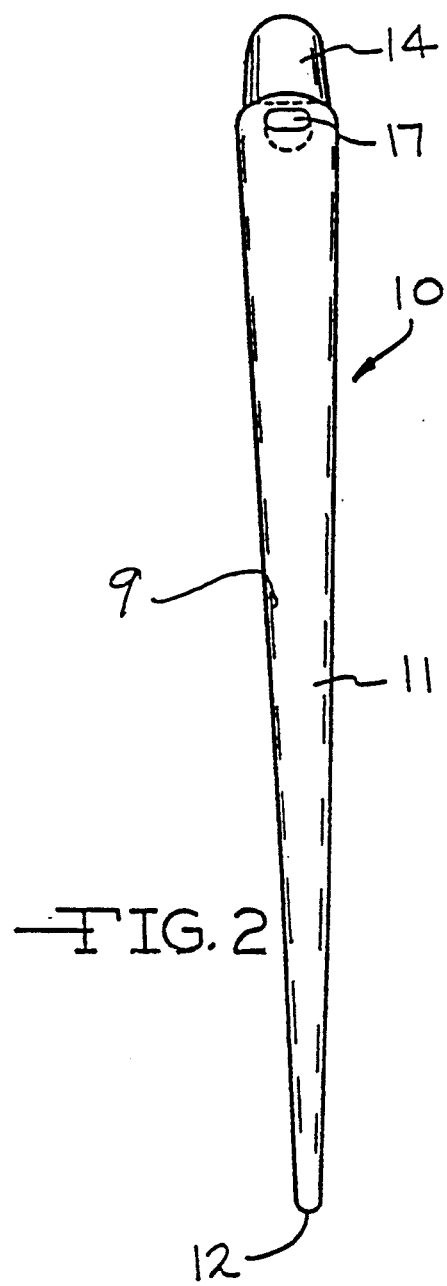
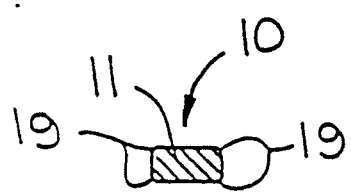
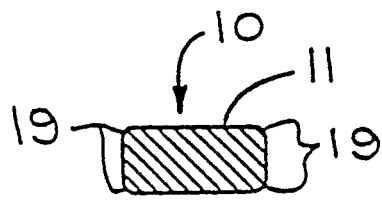

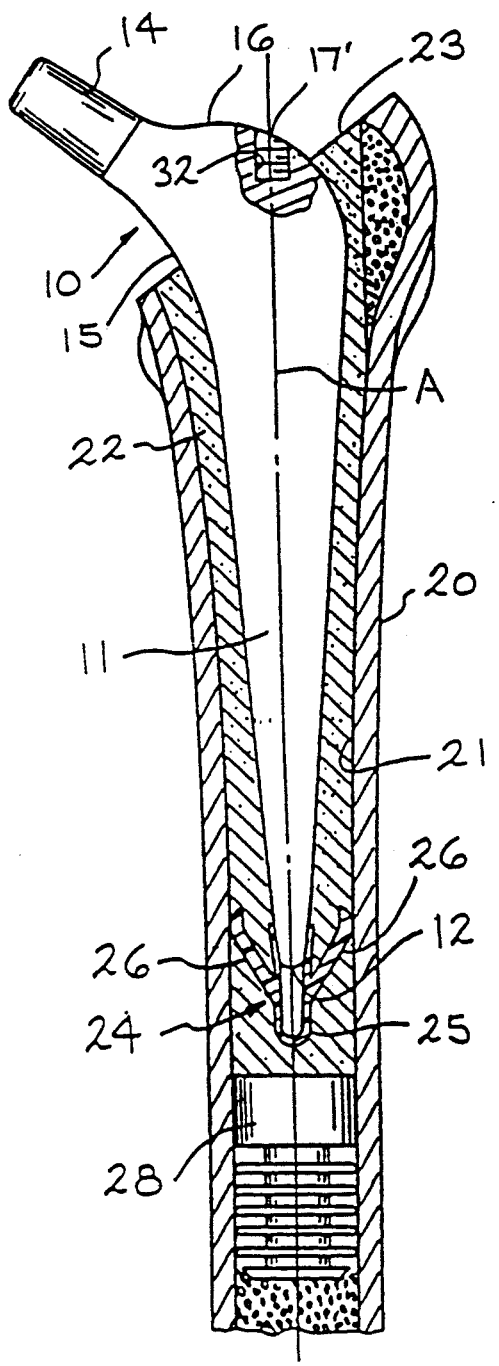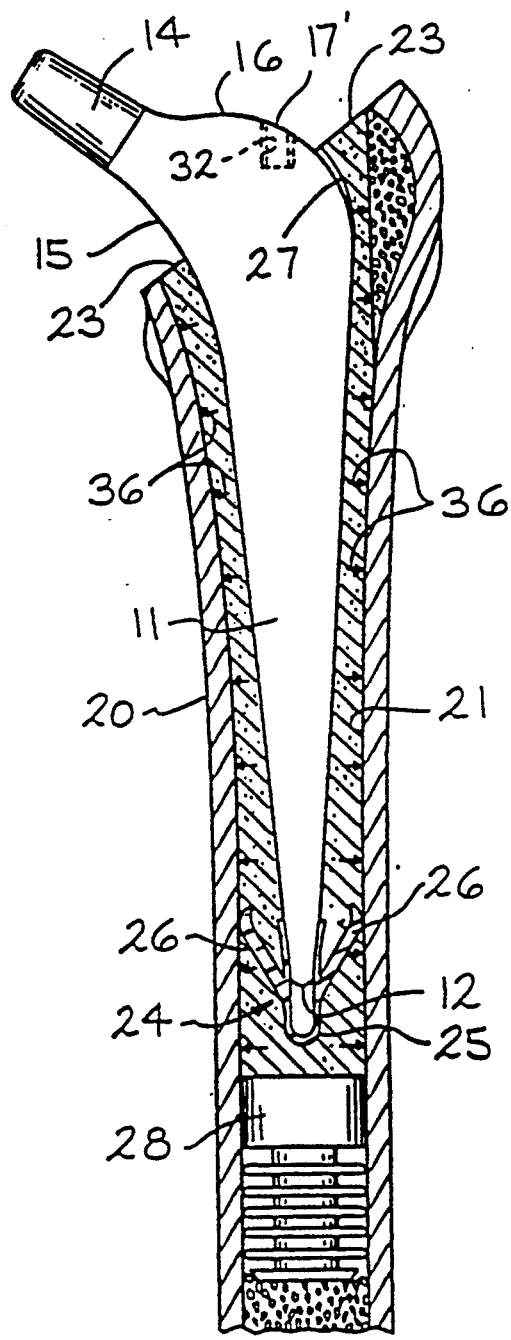

FEMORAL STEM PROSTHESIS

FIELD OF THE INVENTION

This invention relates to a femoral stem prosthesis but more particularly relates to a surface hardened highly polished femoral stem prosthesis.

BACKGROUND OF THE INVENTION

Recently, femoral hip stems have been developed and patented for improving implant fixation in a cemented use which calls for the implant to be highly polished. The highly polished implant is designed to subside within a hardened cement mantle to improve fixation during use. The highly polished surface of the implant prevents or substantially prevents the implant from bonding with the bone cement so that it may shift relative to the cement without abrasion. Preferably, the implant is made from a high strength forged Co-Cr-Mo alloy (ASTM designation F-799) which has its surface polished to a high degree (also known as color buff finish) to provide for a smoothness having a target surface roughness of four microinches. A more thorough understanding of this type of hip stem may be had by a reading of U.S. Pat. Nos. 5,171,275 and 5,171,288 issued on Dec. 15, 1992, to Ling et al and Mikhail et al respectively. U.S. Pat. Nos. 5,171,275 and 5,171,288 are incorporated herein by reference.

SUMMARY OF THE INVENTION

The femoral hip stem of this invention calls for a geometry substantially similar to the implants of the incorporated reference U.S. Pat. No. 5,171,275. The implant of the invention however is formed from a titanium alloy (preferably Ti-6A1-4V) which has been surface hardened and the color buffed to a smoothness similar to the incorporated references. If a titanium alloy implant were merely buffed, as is taught by the incorporated reference, microabrasion between the implant and the cement mantle would rough the surface of the implant. The roughened surface of the implant would become abrasive to the cement mantle and thereby generate wear debris with relative movement between the implant and the cement mantle.

This invention teaches the use of a titanium alloy hip stem which has been surface hardened after buffing. The surface hardening may be accomplished in a variety of known methods such as gas nitriding, ion implantation, or vapor deposition. An acceptable method of surface hardening the implant is illustrated in U.S. Pat. No. 5,192,323 issued to Shetty et al on Mar. 9, 1993 Prior to surface hardening the titanium alloy implant, the implant is buffed to a high degree to a surface roughness of preferably four microinches.

Accordingly, it is an object of the invention to provide a titanium implant being surface hardened and buffed to a high degree.

Another object of the invention is to provide a surface hardened buffed titanium femoral implant in combination with a cement mantle implanted in the canal of a femur wherein the cement mantle encapsulates the stem of such prosthesis in an interfacial relationship which permits subsidence of the titanium stem within the cement mantle without disrupting the interfacial adherence between the cement mantle and the bone.

Other objects of the invention will become apparent upon a reading of the following description taken along with the accompanying drawings.

BRIEF DESCRIPTION OF THE DRAWINGS

FIG. 1 is a front elevational view of the femoral hip joint prosthesis, according to the present invention.

FIG. 2 is an end view of such femoral hip joint prosthesis.

FIG. 3 is a sectional view taken through line 3—3 of FIG. 1;

FIG. 4 is a sectional view taken through line 4—4 of FIG. 1;

FIG. 5 is a sectional view showing the femoral hip joint prosthesis of the present invention immediately after implanting in a patient;

FIG. 6 is a view similar to FIG. 7 showing the femoral hip joint prosthesis after being implanted for a number of years and showing, greatly exaggerated, the effects of subsidence.

DESCRIPTION OF THE PREFERRED EMBODIMENT

Referring now to FIGS. 1 and 2, there is shown a femoral hip joint prosthesis 10 having a stem 11 which is convergently tapered toward a distal end 12 and extending along a first axis of symmetry A to an area of juncture with a neck portion 13 lying on a second axis of symmetry B. Extending from the neck portion 13 is a frustoconically shaped Morse Taper Neck 14 to which may be attached a spherically shaped Morse Taper Head. As is clear from FIG. 1, no collar is provided in the femoral hip prosthesis, but rather the portion of the prosthesis joining the stem 11 to the neck 13 follows a smooth arcuate contour in the area 15 of the included angle between the respective axes of symmetry A and B. The portion of the femoral hip prosthesis 10 opposite the smooth arcuate portion 15, namely, that portion on the outside of the angle between the two axes of symmetry A and B, has an enlarged shoulder 16 in which is formed a dimple or recess 17 for driving the prosthesis into the femur. As can be seen, the dimple 17 is located on the first axis of symmetry A.

An aperture 18 is provided in the area of the neck and shoulder to assist in removing the prosthesis 10 in the event revision is required at some future time.

As can be seen in FIGS. 3 and 4, the stem 11 is tapered in both directions and has rounded corners 19. As pointed out in United Kingdom Patent Specification 1,409,054, such double tapering enhances the extrusion of cement caused by penetration of the stem 11 therein during insertion.

The femoral hip joint prosthesis 10 of the present invention is formed of a titanium alloy, specifically Ti-6A1-4V. The titanium prosthesis is then surface polished to a high degree (also known as a color buff finish) to provide for a smoothness having a target surface roughness of four (4) microinches. The buffed prosthesis 10 is subjected to a surface hardening procedure to form a hardened surface 9 extending into the implant a predetermined amount. The depth of the hardened surface 9 is illustrated in FIGS. 1 and 2 by a broken line. It should be understood and as is more completely explained in the incorporated U.S. Pat. No. 5,192,323, that the surface hardening process is not a coating but rather is an alteration of the mechanical properties of the outer surface of the prosthesis to a preferred depth.

It is the combination of the buffed titanium alloy having its surface polished to the above target and the surface hardening process, coupled with the tapered stem and collarless design which permits the femoral hip prosthesis of the present invention to function in the manner intended without loosening and without causing pain or other adverse mechanical effects in the patient even though there is subsidence of the prosthesis over a period of time. Without the combination of the surface hardening and buff polishing to the above target, the titanium implant would become roughened by micromotion with the cement mantle and thereby create undesired wear debris. Further, the roughened surface may fix the prosthesis to the cement mantle which is in direct contrast to the intended function of the implant. Thus, the present design permits the surface hardened, polished stem to subside within the cement mantle. The taper of the stem permits it to self-tighten upon the slight movement which occurs during the subsidence and engage in the hollow centralizer and yet to do so without pulling the cement mantle and thus avoid disrupting the micro-interlocking at the cement-bone interface. Such design causes the stem to impart primarily compressive forces against the cement mantle, thus transmitting the load to the femur. Transmitting the load in this manner forces the cement mantle continuously snugly and firmly against the interior of the femur to assist in maintaining the integrity of the micro-interlocking at the cement-bone interface.

Referring now to FIG. 7, there is shown the femoral hip joint prosthesis 10 of the present invention immediately followings its implantation in the femur bone 20. As is customary, the femur bone 20 is prepared by reaming a canal 21 into which PMMA or other suitable bone cement is introduced under pressure. Promptly after introduction of the bone cement into the canal 21 and before the cement has had an opportunity to set, the stem 11 of the femoral hip joint prosthesis 10 is inserted into the cement with the result that a cement mantle 22 is formed around the stem 11 up to the arcuate area 15 and a portion of the enlarged shoulder 16. Any excess cement is wiped away leaving an exposed upper end 23. The free or distal end 12 of the stem 11 is engaged in a hollow plastic centralizer 24 which ensures that there will be a sufficient thickness of cement around all portions of the stem. The plastic centralizer 24 includes a cup-shaped pocket 25 having a plurality, preferably 3 or 4 of integrally formed resilient arms 26 sized to engage the interior of the canal 21. Prior to the introduction of the cement into canal 21, a cement restrictor 28 is positioned therein.

Modifications will be readily apparent to those skilled in the art. Accordingly, the present invention should be limited only by the scope of the claims.

We claim:

1. A method for implanting a femoral hip joint prosthesis in a prepared intramedullary canal comprising the step of:
   (a) providing a prosthesis having an elongated stem extending form a proximal end to a distal end and defining a first axis, said proximal end having a neck region which joins the stem at a juncture, said stem having anterior, posterior, medial, and lateral surfaces and said surfaces tapering downwardly from said juncture to said distal end; said neck region defining a second axis disposed at an obtuse angle with the first axis, and said medial surface defining a smooth arcuate path from the stem across the juncture to the neck region and said lateral surface defining an enlarged shoulder proximal said juncture; and said surfaces having a polished finish throughout such that substantially no interfacial bonding will occur between such surfaces and bone cement in contact therewith, said stem being formed of a titanium alloy and said surfaces being surface hardened after polishing such that the hardness of the surfaces is greater than an interior of the prosthesis
   (b) placing cement in said intramedullary canal;
   (c) inserting said prosthesis, distal end first, into said intramedullary canal such that substantially all of said stem is encapsulated within said cement;
   (d) permitting said cement to set forming an interfacial bond with bone surface of said intramedullary canal and a support for said stem; and
   (e) thereafter permitting said stem to subside within said cement without disrupting said interfacial bond.

2. A method for implanting a femoral hip joint prosthesis in a prepared intramedullary canal comprising the steps of:
   (a) providing a prosthesis having an elongated stem extending from a proximal end to a distal end and defining a first axis, said proximal end having a neck region which joins the stem at a juncture, said stem having anterior, posterior, medial, and lateral surfaces and said surfaces tapering downwardly from said juncture to said distal end; said neck region defining a second axis disposed at an obtuse angle with the first axis, and said medial surface defining a smooth arcuate path from the stem across the juncture to the neck region and said lateral surface defining an enlarged shoulder proximal said juncture; and said stem being formed of a titanium alloy and said surfaces being surface hardened such that said surfaces have a hardness greater than an interior of the prosthesis, said surfaces also having a polished finish throughout before being surface hardened such that substantially no interfacial bonding will occur between such surfaces and bone cement in contact therewith
   (b) placing in said intramedullary canal
   (c) inserting said prosthesis, distal end first into said intramedullary canal such that substantially all of said stem is encapsulated within said cement and said distal end is engaged in the open upper end of said centralizer;
   (d) permitting said cement to set forming an interfacial bond with bone surface of said intramedullary canal and a support for said stem; and
   (e) thereafter permitting said stem to subside within said centralizer and within said cement without disrupting said interfacial bond.

3. A method for implanting a femoral hip joint prosthesis in an intramedullary canal comprising the steps of:
   (a) providing a prosthesis having an elongated stem extending from a proximal end to a distal end, said stem tapering from a relatively larger cross-sectional size adjacent said proximal end to a smaller cross-sectional size adjacent said distal end and being formed of a titanium ally and having a polished finish having a surface roughness no greater than 4 microinches and having substantially all surfaces hardened by a surface hardening process after polishing;

(b) placing cement in said intramedullary canal;
(c) inserting prosthesis, distal end first, into said intramedullary canal such that substantially all of said stem is encapsulated within said cement
(d) permitting said cement to set forming an interfacial bond with bone surface of said intramedullary canal and a support for said stem; and
(e) thereafter permitting said stem to subside within said cement without disrupting said interfacial bond.

* * * * *